United States Patent
Briggs et al.

(10) Patent No.: US 6,756,403 B2
(45) Date of Patent: Jun. 29, 2004

(54) METHODS FOR PRODUCING CHIRAL CHROMONES, CHROMANES, AMINO SUBSTITUTED CHROMANES AND INTERMEDIATES THEREFOR

(75) Inventors: Barbara Briggs, Redwood City, CA (US); James Kanter, South San Francisco, CA (US); John J. G. Mullins, San Francisco, CA (US); Gerd Ruhter, Hamburg (DE); Uko Udodong, Indianapolis, IN (US); Milton Zmijewski, Jr., Carmel, IN (US); Daniel Verral, II, Midland, MI (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/297,096
(22) PCT Filed: Jun. 1, 2001
(86) PCT No.: PCT/US01/17980
§ 371 (c)(1),
(2), (4) Date: Jul. 11, 2003
(87) PCT Pub. No.: WO01/94335
PCT Pub. Date: Dec. 13, 2001

(65) Prior Publication Data
US 2004/0053992 A1 Mar. 18, 2004

Related U.S. Application Data
(60) Provisional application No. 60/208,827, filed on Jun. 2, 2000.

(51) Int. Cl.$^7$ ............... A61K 31/35; C07D 311/74
(52) U.S. Cl. ............... 514/456; 549/404; 549/405
(58) Field of Search ............... 549/404, 405; 514/456

(56) References Cited

U.S. PATENT DOCUMENTS

| | | | |
|---|---|---|---|
| 4,026,907 A | 5/1977 | Scott et al. | |
| 5,731,324 A | 3/1998 | Fisher et al. | |

Primary Examiner—Amelia Owens
(74) Attorney, Agent, or Firm—Knobbe, Martens, Olson & Bear LLP

(57) ABSTRACT

Disclosed are process steps and novel processes for producing chromane compositions enriched in at least one (2R or 2S) enantiomer, preferably chroman-2-yl carboxylic acid compounds and chroman-2-yl carboxylic acid esters which are intermediates for producing platelet aggregation inhibitors and/or are themselves potent platelet aggregation inhibitors. Further disclosed are enzymatic processes for resolving chiral intermediates or final products to provide desired enantiomers.

24 Claims, No Drawings

METHODS FOR PRODUCING CHIRAL CHROMONES, CHROMANES, AMINO SUBSTITUTED CHROMANES AND INTERMEDIATES THEREFOR

This is the U.S. national phase under 35 U.S.C. §371 of International application PCT/US01/17980, published in English, filed Jun. 1, 2001, which claims priority to U.S. Provisional Application No. 60/208,827, filed Jun. 2, 2000.

FIELD OF THE INVENTION

This invention relates to novel processes for producing chromane compounds, preferably chroman-2-yl acetic acid compounds and amino substituted chroman-2-yl acetic acid esters which are intermediates for producing platelet aggregation inhibitors and/or are themselves potent platelet aggregation inhibitors. It further relates to processes for resolving chiral intermediates or final products to provide desired enantiomers.

BACKGROUND OF THE INVENTION

One process for making chromanes from coumarin derivatives is described in U.S. Pat. No. 5,731,324 at pages 101–103. The unprotected amino derivative bicyclic compound is shown on page 147. However, that process involves chromatography as a purification step, which does not scale well commercially.

SUMMARY OF THE INVENTION

In accordance with one preferred embodiment, there is provided a process for making a compound, or a salt thereof, having a general formula:

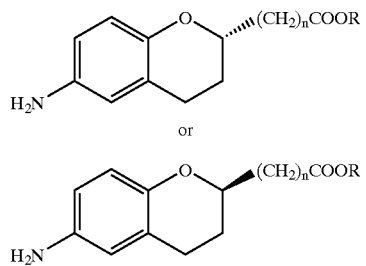

or wherein R is $C_1$–$C_8$ alkyl and n=0 to about 3. The method comprises (a) through (f) below:

(a) reacting phenol and beta-keto glutaric acid in $H_2SO_4$/ Ethanol with heat, followed by pouring the reaction mixture onto ice water, extracting into organic solvent and evaporating as follows:

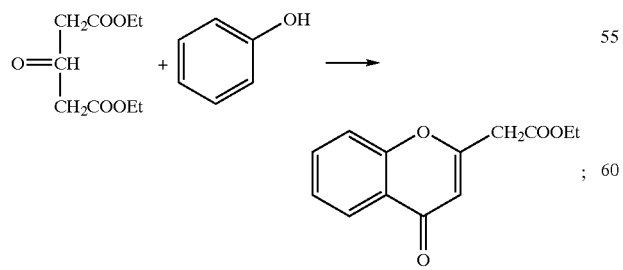

(b) hydrogenating the chromenone product from (a) above to produce the corresponding chromanone:

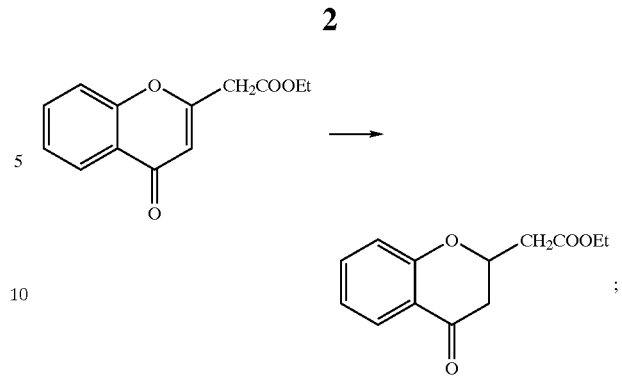

(c) nitrating the chromanone from (b) as follows:

(d) resolving the racemic mixture using a lipase enzyme, as follows:

(e) hydrogenating the 4-carbon to remove the oxo group and convert the nitro group to an acetamido group as follows:

(f) acidifying the product from (e) above to recover the amine followed by addition of concentrated HCl to produce the HCl salt as follows:

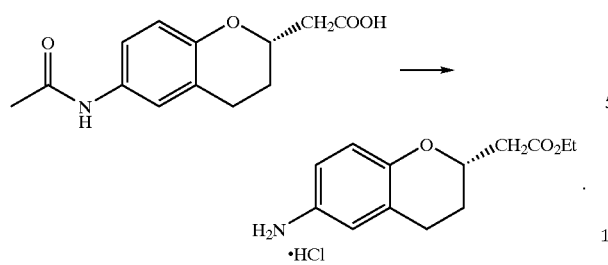

In accordance with one preferred embodiment, there is provided a process for making a compound, or a salt thereof, having a general formula:

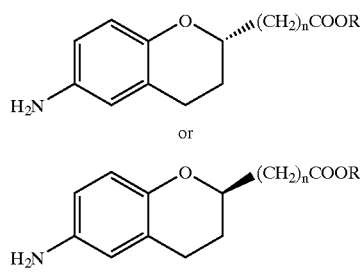

wherein R is $C_1$–$C_8$ alkyl and n=0 to about 3. The method comprises (a) through (g) below:

(a) reacting 2-hydroxyacetophenone and diethyloxalate in the presence of sodium ethoxide followed by addition of concentrated sulfuric acid to make the bicyclic ring system as follows:

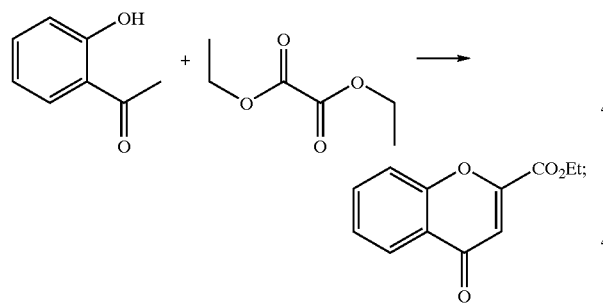

(b) hydrogenating the chromen-4-one to form the chromen-4-one as follows:

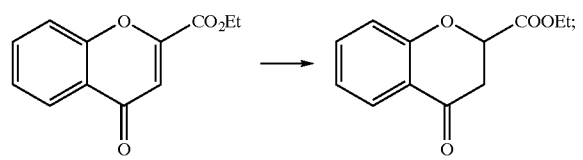

(c) performing a chain extension by first making the free acid, followed by reacting with borane-methyl sulfide complex to form the 2-hydroxymethyl derivative, followed by replacing the hydroxy group with a tosyl group and reacting the tosyl derivative with a cyanide salt to form a 2-cyano derivative, followed by acidifying the cyano derivative in concentrated acid and esterifying the 2-acid group as follows:

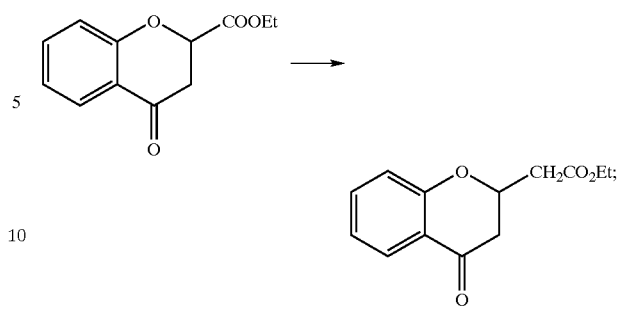

(d) nitrating the product from (c) above to form the 6-nitro group as follows:

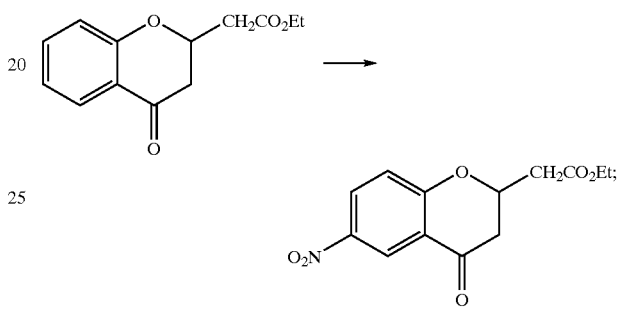

(e) resolving the racemic mixture using a lipase enzyme, as follows:

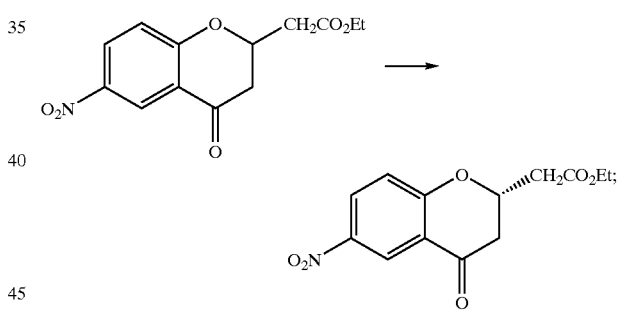

(f) hydrogenating the 4-carbon to remove the oxo group and convert the nitro group to an acetamido group as follows:

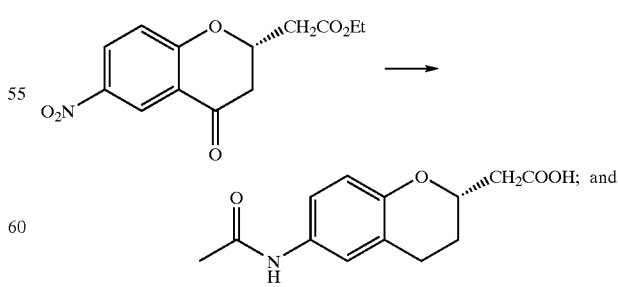

(g) acidifying the product from (f) above to recover the amine followed by addition of concentrated HCl to produce the HCl salt as follows:

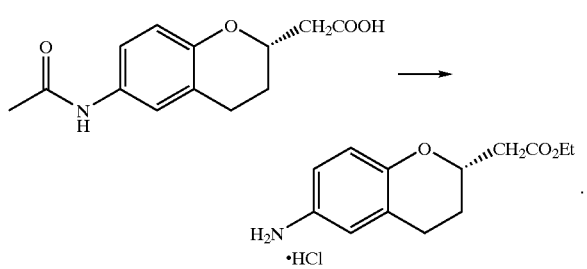

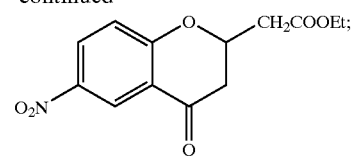

In accordance with one preferred embodiment, there is provided a process for making a compound, or a salt thereof, having a general formula:

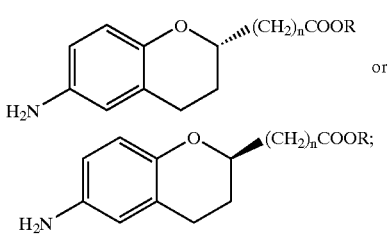

wherein R is $C_1$–$C_8$ alkyl and n=0 to about 3. The method comprises (a) through (e) below:

(a) reacting nitrophenol and diethyl ester of maleic acid with methane sulfonic acid under heating as follows:

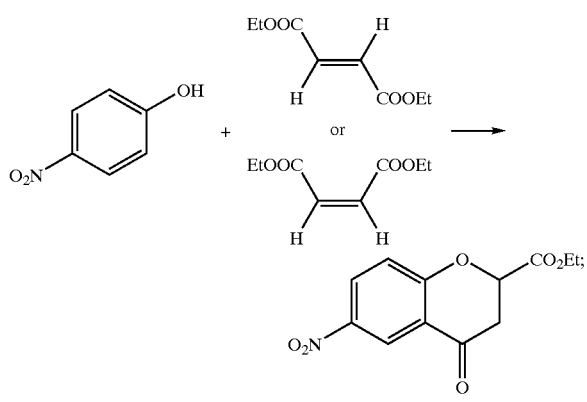

(b) performing a chain extension by first making the free acid, followed by reacting with borane-methyl sulfide complex to from the 2-hydroxymethyl derivative, followed by replacing the hydroxy group with a tosyl group and reacting the tosyl derivative with a cyanide salt to form a 2-cyano derivative, followed by acidifying the cyano derivative in concentrated acid and esterifying the 2-acid group as follows:

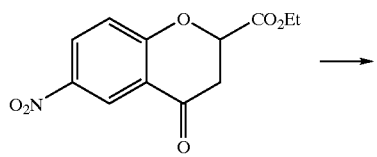

(c) resolving the racemic mixture using a lipase enzyme, as follows:

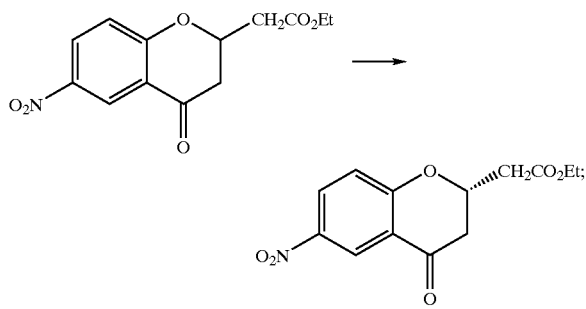

(d) hydrogenating the 4-carbon to remove the oxo group and convert the nitro group to an acetamido group as follows:

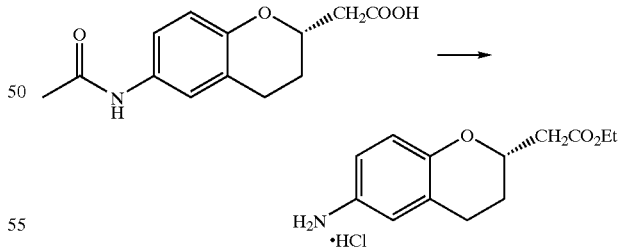

(e) acidifying the product from (d) above to recover the amine followed by addition of concentrated HCl to produce the HCl salt as follows:

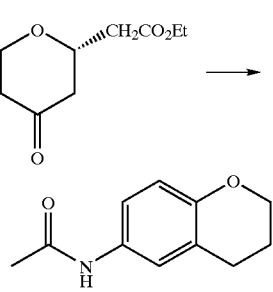

In accordance with one preferred embodiment, there is provided a process for making a compound, or a salt thereof, having a general formula:

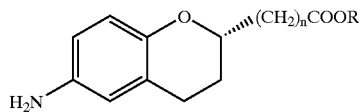

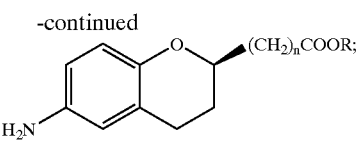

wherein R is $C_1$–$C_8$ alkyl and n=0 to about 3. The process comprises (a) through (g) below:

(a) nitrating the chromen-4-one at the 6-position as follows:

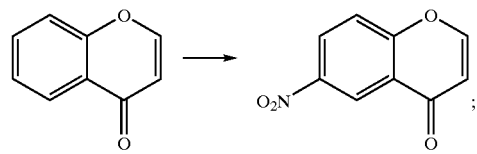

(b) reacting the product from (a) above with TBSOTf to form a benzopyrillium salt as follows:

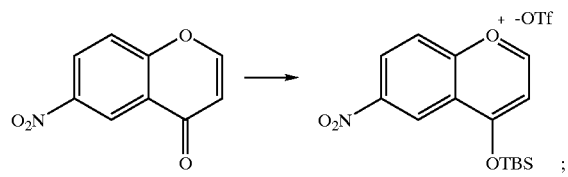

(c) adding the ketene enol to the benzopyrillium salt from (b) above as follows:

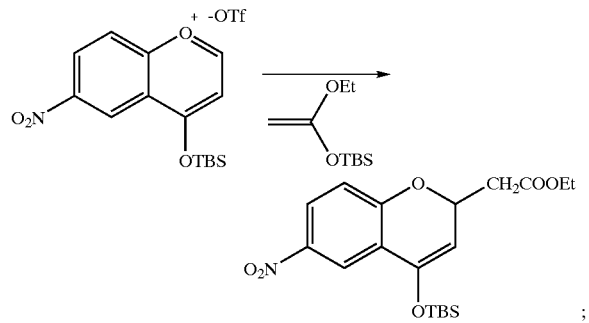

(d) acidifying the product from (c) above to complete the addition of the substituent at the 2-position on the 6-nitro-4-oxochromane ring as follows:

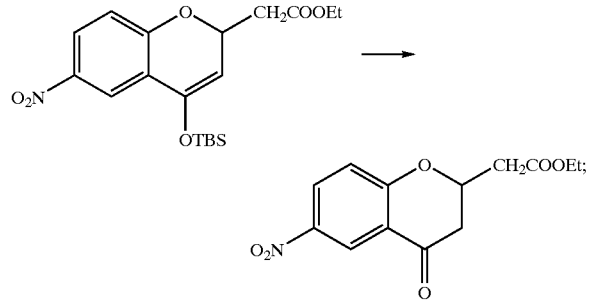

(e) resolving the racemic mixture using a lipase enzyme, as follows:

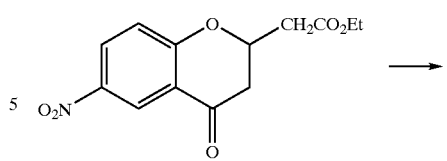

(f) hydrogenating the 4-carbon to remove the oxo group and convert the nitro group to an acetamido group as follows:

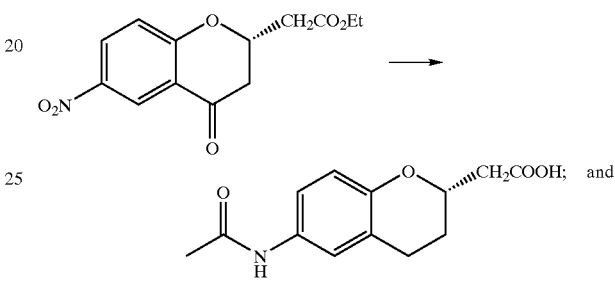

(g) acidifying the product from (f) above to recover the amine followed by addition of concentrated HCl to produce the HCl salt as follows:

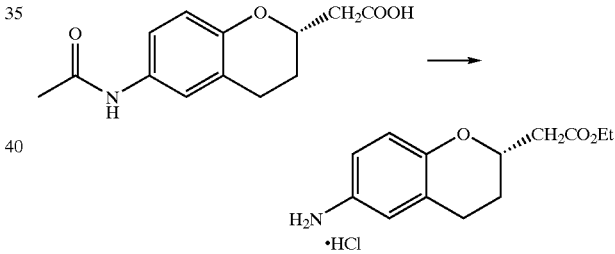

The compositions formed according to the above methods preferably comprise about 75% to about 100% of a single (2R) or (2S) enantiomer of 6-aminochroman-2-yl acetic acid or an ester thereof.

In preferred embodiments, the lipase is from *Pseudomonas cepacia*, is the PS 30 lipase, is stabilized by cross-linking with alpha keto glutarate and the like, or is the stabilized PS 30 enzyme ChiroCLEC-PC.

DETAILED DESCRIPTION OF THE PREFERRED EMBODIMENTS

In view of the shortcomings of the known process mentioned above, there is a need for improved processes for producing compounds that are useful as intermediates in processes for producing platelet aggregation inhibitors. There is a particular need for Improved processes for making compounds having the phenyl ring of the benzopyrans substituted by an amino group or a protected amino group. Such intermediates are useful for coupling with a carbonyl group to produce a carboxamide link and result in compounds that are useful platelet aggregation inhibitors or intermediates for forming platelet aggregation inhibitors.

Also needed is a process to produce relatively inexpensively large quantities of chromone intermediates that are useful for being resolved by conventional processes to produce benzopyran or chromane derivatives wherein the chiral center at the two position of the saturated pyran ring portion of the bicyclic ring structure can be resolved into racemic mixtures (R/S) that are enriched with one of the R or S enantiomers or to produce substantially pure compositions of a single enantiomer (R or S enantiomer). Due to inherent losses of up to 50% or more of the starting materials (assuming a 50/50 R/S racemate) during enantiomeric resolution, there is a need for a process which is efficient enough to be scaled to an industrial level for inexpensively producing large quantities of a desired intermediate compound or large quantities of final chroman-2-yl acetic acid ester compounds that are useful in the anticoagulant field.

Accordingly, there continues to be a need for a process that is adaptable to commercially scaleable production of such chromanes. One or more of the foregoing needs may be met using the processes described herein and the compounds and intermediates made thereby.

The disclosure herein presents novel processes for producing chromane compounds, preferably chroman-2-yl acetic acid compounds and amino substituted chroman-2-yl acetic acid esters which are intermediates for producing therapeutic agents, or are themselves therapeutic agents, for disease states in mammals that have disorders caused by or Impacted by platelet dependent narrowing of the blood supply.

In particular, disclosed are processes that utilizes a Simonis Chromone cyclizing step with a phenol starting material and glutarate ketone under acidic condition ($P_2O_5$, phosphorous oxychloride or $H_2SO_4$). Preferably, sulfuric acid and absolute ethanol are utilized to produce the acetic add ethyl ester at the 2-position as follows:

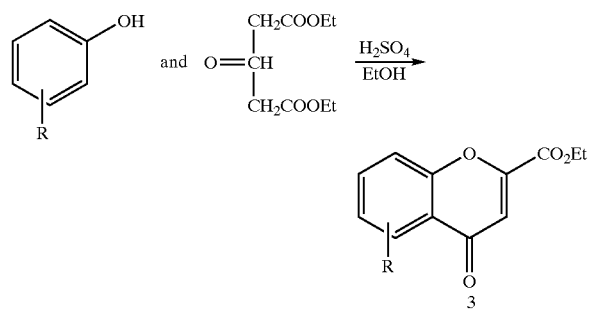

wherein R is a substituent on the phenyl or benzene ring and R is a nitro group or an amino group (or a protected amino group such as a benzamido or acetamido group) or a group that can be converted to a nitro or amino group (e.g., hydrogen or halogen). Preferably, the 2-carboxylic acid group is esterified with an ethyl group and the R group on the benzene or phenyl portion is hydrogen, halogen or a $NO_2$ group Most preferably, the R group is a hydrogen atom.

The double bond of the oxo-pyran portion of the bicyclic ring is preferably reduced by hydrogenation processes such as hydrogen and Pd/C, or the like as follows:

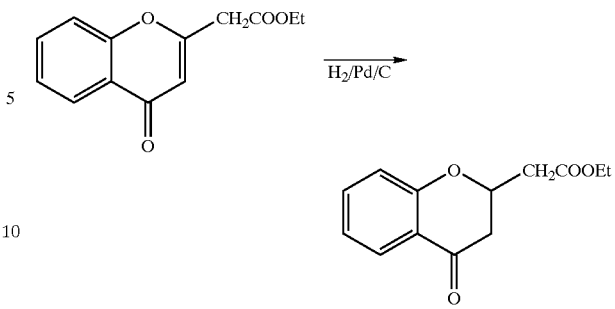

to produce the chromone product from the chromenone compound. The presence of ethyl acetate, ethanol and the like as a solvent can minimize the formation of a hydroxyl group from the carbonyl group in the ring. In any event, a standard reaction to covert a hydroxyl group to a ketone (carbonyl) may be alternatively utilized if a hydroxyl group is desired. The resulting compound can be substituted with a desired R substituent in the phenyl ring, preferably with a 6-position $NO_2$ group, by reacting the chromone compound with a nitrating agent such as a metallic nitrate in a mineral acid. Preferably, potassium nitrate is utilized with sulfuric acid at a temperature of from 0° C. to room temperature, but any. nitration procedure may be used. Due to steric and electronic directing, a very high amount of the 6-position nitro compound is obtained and the reaction may be monitored with HPLC, for example, to determine completion. Work-up is done by crystallization, e.g., ethyl acetate or toluene, to favor a particular position isomer.

The nitrating reaction may be illustrated as follows:

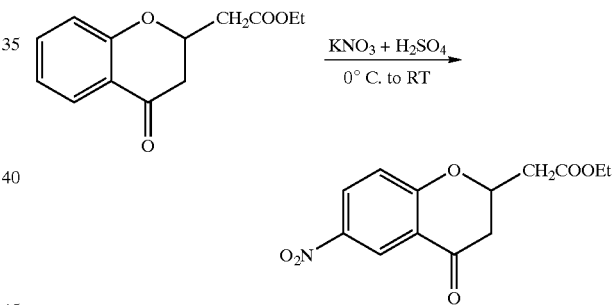

to provide a racemic ethyl (6-nitro-4-oxochroman-2-yl) acetate as shown above. Also, as is clear from the above discussion, If R is a nitro group prior to the hydrogenation step, an amino group on the phenyl ring results from the hydrogenation with the Pd/C, or the like. Since certain lipases may favor the hydrolysis of the acetic acid ester when the nitro group is present on the phenyl ring, it is preferred that the nitro group be added to the phenyl ring after the hydrogenation step is completed. The 6-position racemates, including the preferred 6-nitro compound, may be generically illustrated as follows:

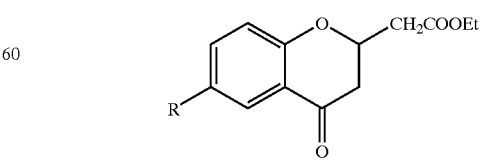

wherein R is a nitro group, an amino group or a protected amino group, such as an acetamido or benzamido group. The individual enantiomers of the racemate can be resolved as set forth below.

Alternatively, to avoid a hydrogenation step prior to nitration, the racemate set forth above can be produced via a benzopyrilium salt by treating a 6-nitro-4-oxo-2-chromene nucleus with TBSOTf, and subjecting the resulting intermediate to a silyl enol ether hydrolysis. The 6-nitro-chromone nucleus is available commercially or can be produced, for example, by nitrating the chromone (4-oxo-2-chromene) at room temperature (Aldrich Catalog Number 19922-2). The nitration step may be illustrated as follows:

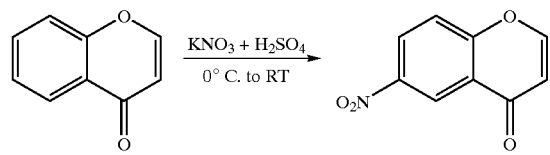

to selectively produce the 6-nitro-chromone nucleus in a high yield, since the electronic nature of chromone nucleus favors the placement of the nitro group in the 6 position on the ring. A benzopyrilium salt is then produced from this chromone nucleus as follows:

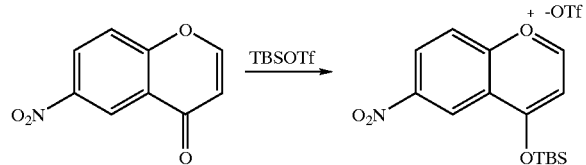

Further, the silyl ketene acetal reactant can be produced from the acetic acid ethyl ester and TBSOTf by using standard methods in the silyl ketene acetal art and reacted with the benzopyrilium salt that is set forth above, which was obtained from the 6-nitrochromone intermediate. Reaction of the salt and the silyl ketene acetal are illustrated as follows:

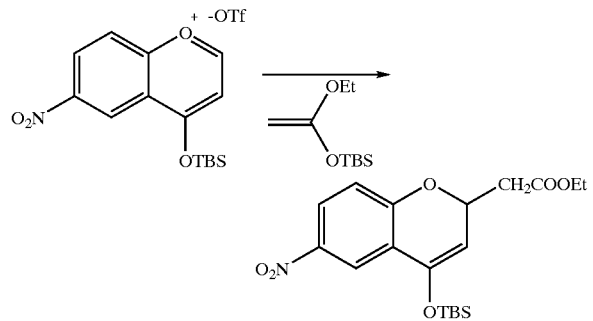

Acidifying the above compound with aqueous HCl, or the like results in the desired racemate, 6-nitro-4-oxochroman-2-yl-acetic acid (ethyl ester), which can be resolved in the same manner as the racemate produced by the Simonis Chromone cyclization procedure, see below.

The overall yield from the benzopyrillium salt to the racemate as set forth in the above alternative to the Simonis Chromone cyclization procedure is quite good, and is usually from about 88–95% yield. One embodiment, which summarizes the above reaction steps as well as enzymatic resolution of the racemate, is set forth below in Scheme IV.

One might note that while the chromone and 6-nitro-chromone compounds described above are standard Items of commerce, routine methods exist in the art for producing such starting materials. Other obvious variations and permutations of the above benzopyrilium salt procedure will be readily apparent to one of ordinary skill in the art in view of the discussion herein and are considered to be within the scope of the disclosure.

A chirally selective lipase such as the Altus, Inc. ChiroCLEC-PC lipase, or the like, may be utilized to resolve the ethyl 2-(6-nitro-4-chromanone)acetate racemate, regardless of whether it is produced by the Simonis Chromone cyclization or via the above benzopyrilium salt process. In the case where the nitro compound is utilized 98.5 percent of the acid formed corresponds to one enantiomer. Crystallization, or other standard separation procedures, may be utilized to separate the acid from the ester and result in a substantially pure or enriched composition of a single enantiomer. Depending upon the desired enantiomer, the crystals or the supernatant may be chosen to be used for further processing.

The undesired isomer may be recycled by using a racemization step followed by re-exposure of the resulting racemate to the lipase. The formation of a racemate from a single enantiomer is accomplished by exposing the enantiomer to a basic alcoholic solution such as a sodium or potassium ethanolate solution. Other procedures which open the ring at the ring oxygen of the chromone and then reclose it may also be utilized to produce a racemate from a single enantiomer. By repeating the resolution and racemate forming steps, a higher overall yield may be obtained. The racemate forming step may be illustrated as follows:

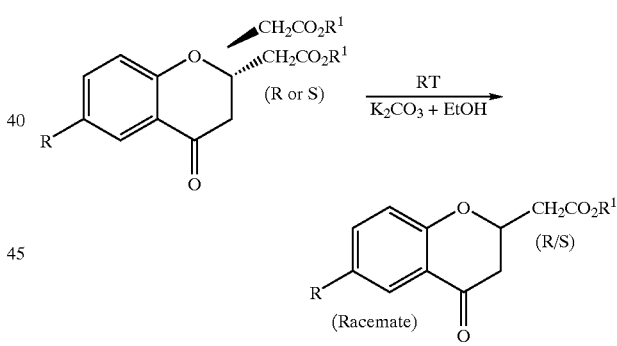

wherein, as illustrated, a catalytic amount of potassium carbonate or similar catalytic base in $R^1OH$ (preferably EtOH) is utilized for 1–3 days at room temperature, saponified with aqueous 1N NaOH in $R^1OH$ for 3 hours. After acidification with 1N HCl, the racemic acid may be crystallized out, washed, and re-esterified with an acidic ethanol solution. The resulting ester racemate can then be recycled by exposure to the lipase to obtain a higher yield of the desired single enantiomer with respect to the initial amount of racemate starting material.

After the resolution of the enantiomers, the 4-oxo group can be removed from the (R) or (S) enantiomer chromone compound and the R group can be converted to an amino group by a simple hydrogenation reaction. Preferably, hydrogen gas and a Pd/C catalyst, or the like, are used to produce a substantially pure single enantiomer of a (2 R or S) chroman-2-yl)acetic acid ester having the phenyl portion substituted as indicated above,: preferably in the 6-position. For example, glacial acetic acid and 30–60 psi of hydrogen at 40–80° C. in the presence of a catalyst such as palladium on carbon may be utilized in a hydrogenator. The reaction can be monitored with HPLC to determine the completion of the hydrogenation. Molecular sieves may optionally be used as well.

Such a hydrogenation reaction is exemplified as follows:

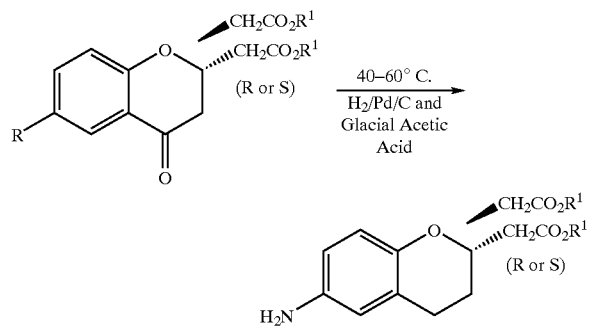

wherein, the amino group can be in the form of a mineral acid salt by addition of an acidic alcohol solution to the compound. Further, if the hydrogenation reaction results in creation of the free acid, it can be converted, to the desired ester by treatment with an appropriate ester-forming alcohol in sulfuric acid followed by exposure to a mineral add alcohol solution to provide the mineral acid salt of the amino group.

Non-limiting Illustrative Scheme I, set forth below, comprises the process steps outlined directly below which may also include further initial starting steps to produce the starting materials which are commercially available or further processing steps which modify the amino group to comprise a desired functional group, such as groups described in the anti-coagulation field. Amino coupling reactions are well-known in the art. Moreover, specific steps that are set forth in the preferred embodiment reaction scheme below are described in the examples. The reaction products are isolated and purified by conventional methods, typically by solvent extraction into a compatible solvent Preferred solvents are lower alkane ethers and alcohols; ethyl ether and isopropyl alcohol are preferred for solvent extraction or recrystallization procedures. Esters of carboxylic add side groups may be formed that permit selective separation of the R and S enantiomers by use of hydrolysis with a lipase, solvent extraction or recrystallization. The products may be further purified by column chromatography or other appropriate methods.

Scheme I
Simonis Chromone Cyclization + Enzymatic Resolution

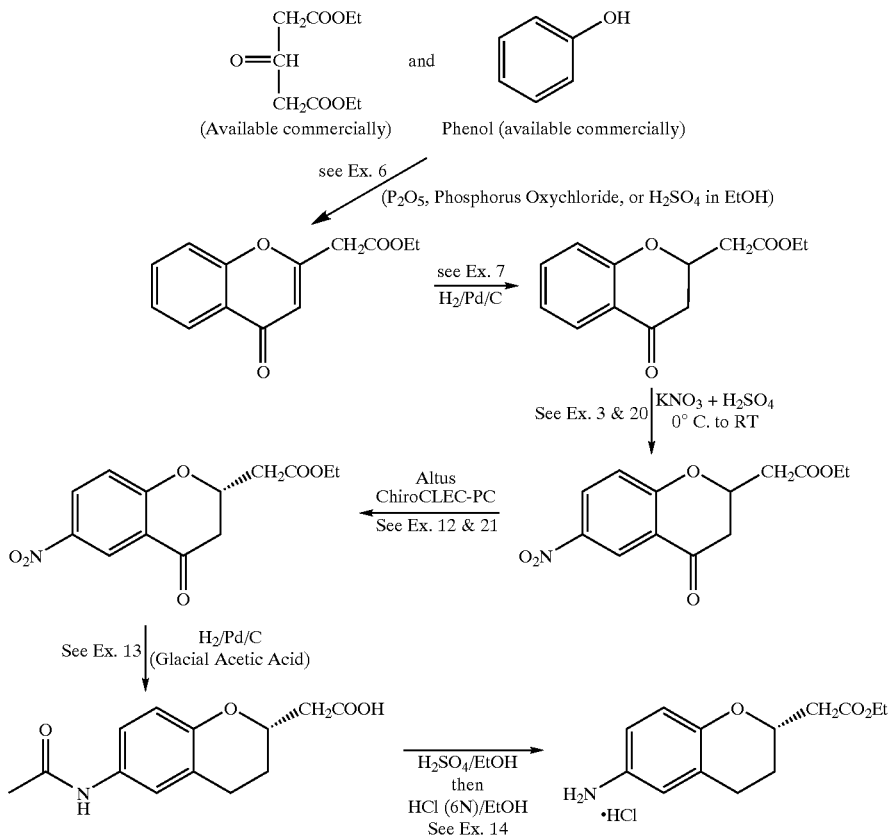

Alternatively, a corresponding 6-nitro-4-oxo-chroman-2-yl carboxylic acid compound can be produced and esterified by using a 5-nitro-acetophenone starting material and the reaction shown in the J. Med. Chem, Vol. 15, No. 8 (1972) or by nitration of the compound described in the referenced article (see Scheme II, below). Additionally, the 6-nitro-4-oxo-chroman-2-yl carboxylic acid ester can be made by reacting nitrophenol and the diethyl ester of maleic add, for example (see Scheme III, below).

For example, the carboxylic acid group of the desired enantiomer can be extended to an acetic acid group by reducing the carboxylic acid side group to form a methanol side chain followed by extending its length via a potassium cyanate reaction and the like. After the side extension reaction is completed, the racemate of the 6-nitro-4oxo-chroman-2-yl carboxylic acid ester can be resolved by the above process utilizing the Altus ChiroCLEC-PC enzyme (or any other acceptable lipase). PS 30 and functionally similar enzymes can also be utilized, and then extended to an acetic acid ethyl ester side chain after the resolution.

After resolution, the 4-oxo group is removed and the 6-nitro group is reduced to an amino group by a hydrogenation step. For example, a hydrogenator loaded with the compound in ethanol or acetic anhydride in the presence of 10% palladium on carbon at 40–60° C. and 40–60 psi of hydrogen can be used for the reduction step, with or without the presence of molecular sieves. The progress of the reaction can be monitored via HPLC.

Additional non-limiting schemes are set forth below:

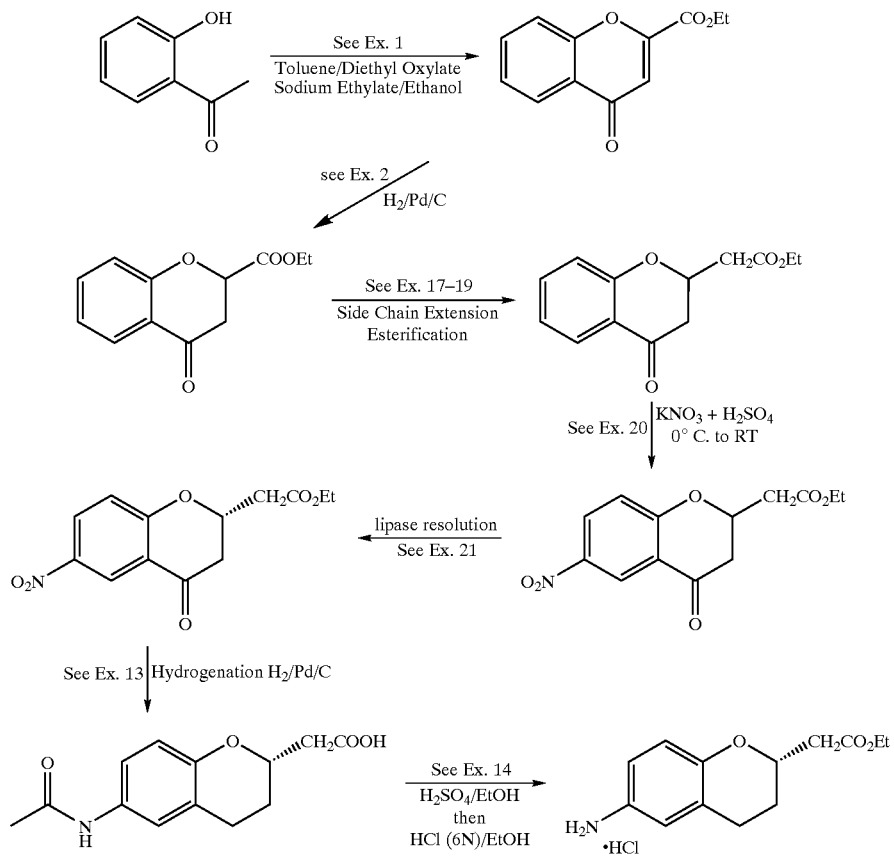

Scheme II

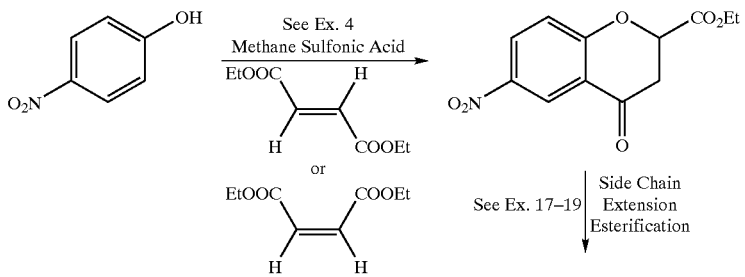

Scheme III

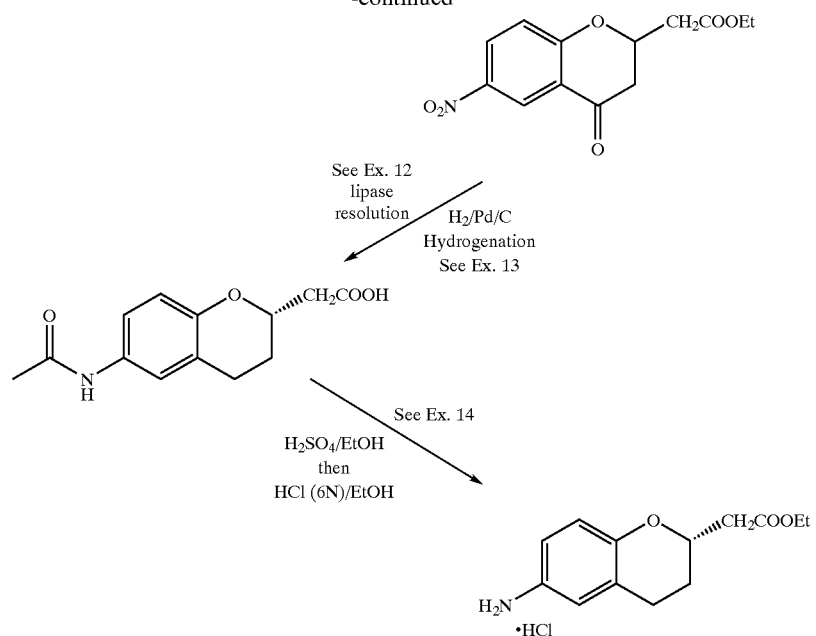
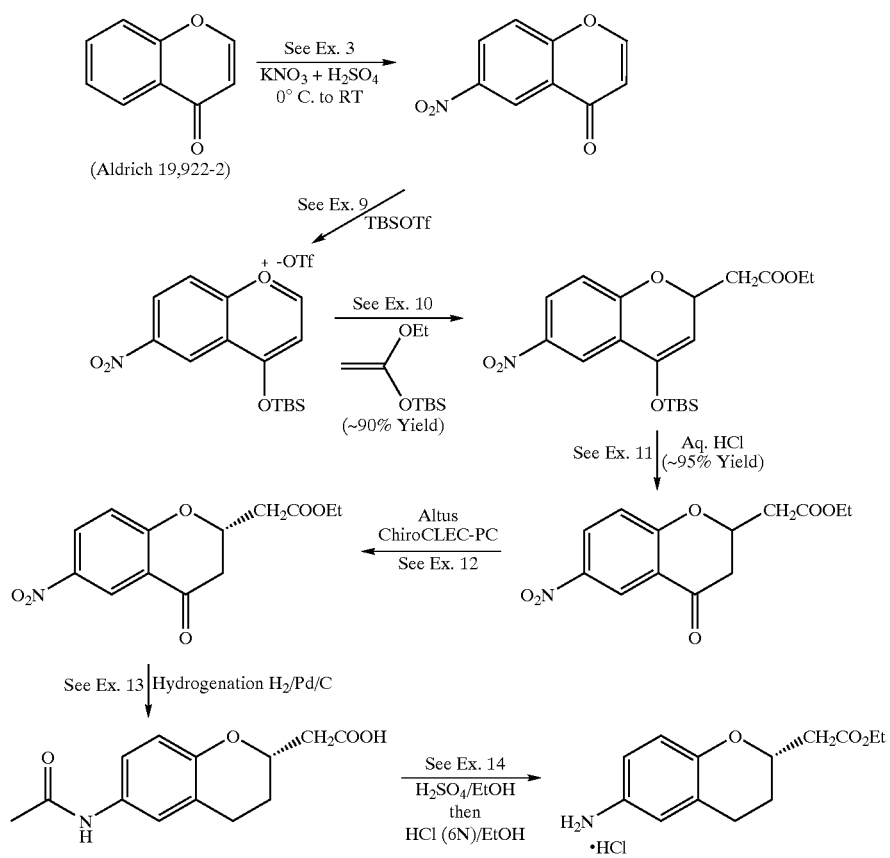
In other embodiments, the order of some of the reactions in the schemes may be changed, and additional steps of protecting, deprotecting, nitrating, hydrolyzing, esterifying, and the like may be added to the schemes at various points. Such minor alterations are within the scope of the disclosure herein. Although the esters shown are primarily ethyl esters, other esters may be made, either by use of different solvents and/or reagents in the initial formation reactions or by transesterificaton.

The starting materials used in the disclosed processes are commercially available from chemical vendors such as Aldrich, Lancaster, TCI, Bachem Biosciences, and the like, or may be readily synthesized by known procedures including those present in the chemical literature, or may be made by using procedures such as indicated above.

Reactions are carried out in standard laboratory glassware and reaction vessels under reaction conditions of standard temperature and pressure, except where it is otherwise indicated, or where use of non-STP conditions for a procedure is known in the art. Some procedures, reactions, and/or workups which are well known in the art or which are readily available in standard reference texts in the art, including Beilstein and Fieser and Fieser, may not be presented herein owing to their stature of being within the knowledge of one of ordinary skill. Further, the above procedures of the claimed invention processes may be carried out on a commercial scale by utilizing reactors and standard scale-up equipment available in the art for producing large amounts of compounds in the commercial environment. Such equipment and scale-up procedures are known to the ordinary practitioner in the field of commercial chemical production.

During the synthesis of these compounds, amino or acid functional groups may be protected by blocking groups to prevent undesired reactions with the amino group during certain procedures. Procedures for such protection and removal of protecting groups are routine and well known to the ordinary practitioner in this field.

Enantiomeric Resolution and Acid Salt Formation

When a reaction results in the production of racemic chroman-2-yl carboxylic acids and esters, these racemates are preferably resolved to produce a mixture enriched in one of the R or S enantiomers or completely resolved into a substantially pure composition of one of the enantiomers. Examples of processes for resolving the racemic mixtures are provided herein and/or are known to those skilled in the art Additionally, processes for the formation of acid addition salts such as the hydrochloride salt of the 6-position amino acid group on the chromane nucleus are known in the art. Other such salts are also envisioned.

Uses of Compounds

As mentioned above, the compounds produced according to preferred embodiments find utility as intermediates for producing therapeutic agents or as therapeutic agents for disease states in mammals, including those which have disorders that are due to platelet dependent narrowing of the blood vessels, such as atherosclerosis and arteriosclerosis, acute myocardial infarction, chronic stable angina, unstable angina, transient ischemic attacks and strokes, peripheral vascular disease, arterial thrombosis, preeclampsia, embolism, restenosis following angloplasty, carotid endarterectomy, anastomosis of vascular grafts, and etc. These conditions represent a variety of disorders thought to be initiated by platelet activation on vessel walls.

Platelet adhesion and aggregation is believed to be an important part of thrombus formation. This activity is mediated by a number of platelet adhesive glycoproteins. The binding sites for fibrinogen, fibronectin and other clotting factors have been located on the platelet membrane glycoprotein complex IIb/IIIa. When a platelet is activated by an agonist such as thrombin, the GPIIb/IIIa binding site becomes available to fibrinogen, eventually resulting in platelet aggregation and clot formation. Thus, intermediate compounds for producing compounds that effective in the inhibition of platelet aggregation and reduction of the incidence of clot formation are useful intermediate compounds.

The compounds produced according to preferred embodiments may also be used as intermediates to form compounds that may be administered in combination or concert with other therapeutic or diagnostic agents. In certain preferred embodiments, the compounds produced by the intermediates according to the present invention may be co-administered along with other compounds typically prescribed for these conditions according to generally accepted medical practice such as anticoagulant agents, thrombolytic agents, or other antithrombotics, including platelet aggregation inhibitors, issue plasminogen activators, urokinase, prourokinase, streptokinase, heparin, aspirin, or warfarin. The compounds produced from the intermediates may act in a synergistic fashion to prevent reocclusion following a successful thrombolytic therapy and/or reduce the time to reperfusion. Such compounds may also allow for reduced doses of the thrombolytic agents to be used and therefore minimize potential hemorrhagic side-effects. Such compounds can be utilized in vivo, ordinarily in mammals such as primates, (e.g. humans), sheep, horses, cattle, pigs, dogs, cats, rats and mice, or in vitro.

Coupling Reaction of the Hydrochloride Salt Intermediate Compounds

The above compounds produced according to preferred methods may be isolated and further reacted to substitute a desired group for one or more of the hydrogen atoms on the amino group by a coupling reaction. Particularly preferred is a coupling reaction of the amino group with an acyl halide compound. For example, compounds such as 5-amidino-thiophen-2-yl carboxylic acid derivatives (or an acyl halide such as the acyl chloride) and 4-amidinobenzoyl chloride may be coupled to ethyl (2S)-(6-amino-chroman-2-yl) acetate (or its hydrochloride salt) to form ethyl (2S)[6-(5-amidino-2-thiophenoyl)amino-chroman-2-yl]acetate and ethyl (2S)-[6-(4-amidinophenyl) carbonylamino]chroman-2-yl} acetate, or other similar compounds or their derivatives which are known platelet aggregation inhibitors. For examples of such platelet aggregation inhibitors, see U.S. Pat. No. 5,731,324. The ring portion of the above amidino-aroyl or amidino-heteroaroyl derivatives may be substituted by groups such as methyl, ethyl, fluoro, iodo, bromo, chloro, methoxy, ethyoxy, and the like which results in compounds that are known platelet aggregation inhibitors. Standard coupling procedures may be utilized, but procedures utilizing reaction mixtures the compounds, in salt form, are suspended in solvents such as acetonitrile, toluene, or the like, are preferred.

The compound formed from the coupling reaction may be used as either the salt or the free base, and may be readily interconverted between the two forms by using procedures which include-those known in the art as well as reacting the compound with one or more molar equivalents of the desired acid or base in a solvent or solvent mixture in which the salt is insoluble, or in a solvent like water after which the solvent is removed by evaporation, distillation or freeze drying. Alternatively, the free acid or base form of the product may be passed over an ion exchange resin to form the desired salt, or one salt form of the product may be converted to another using the same general process. The free base or salts may be purified by various techniques such as recrystallization in a lower alkanol such as methanol, ethanol, propanol, isopropanol and the like, for example, or a mixture thereof. In preferred embodiments, the compound is recovered as the hydrochloride salt and the recrystallization solvent is a 90/10–10/90 mixture of ethanol and isopropanol. Non-toxic and physiologically compatible salts are preferred, although other types of salts may also be used, such as in the processes of Isolation and purification.

Compositions and Formulations

Diagnostic and therapeutic applications of the compounds formed by procedures disclosed herein, including the aforementioned coupling reactions, will typically utilize formulations wherein the compound, or a pharmaceutically acceptable salt, solvate, or prodrug, is combined with one or more adjuvants, excipients, solvents, or carriers. The formulations may exist in forms including, but not limited to tablets, capsules or elixirs for oral administration; suppositories; sterile solutions or suspensions for injectable or parenteral administration; or incorporated into shaped articles. Subjects in need of treatment (typically mammalian) using the compounds of this invention can be administered dosages that will provide optimal efficacy. The dose and method of administration will vary from subject to subject and be dependent upon such factors as the type of mammal being treated, its sex, weight, diet, concurrent medication, overall clinical condition, the particular compounds employed, the specific use for which these compounds are employed, and other factors which those skilled in the medical arts will recognize.

Formulations are prepared for storage or administration by mixing the compound, or a pharmaceutically acceptable salt, solvate or prodrug thereof, having a desired degree of purity with physiologically acceptable carriers, excipients, stabilizers etc., and may be provided in sustained release or timed release formulations. Acceptable carriers or diluents for therapeutic use are well known in the pharmaceutical field, and are described, for example, in Remington's Pharmaceutical Sciences, Mack Publishing Co., (A. R. Gennaro edit. 1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinylpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counter ions such as sodium and/or nonionic surfactants such as Tween, Pluronics or polyethyleneglycol.

Dosage formulations to be used for parenteral administration are preferably sterile. Sterility is readily accomplished by filtration through sterile membranes such as 0.2 micron membranes, or by other conventional methods known to those skilled in the art. Formulations are preferably stored in lyophilized form or as an aqueous solution. The pH of such preparations are preferably between 3 and 11, more preferably from 5 to 9 and most preferably from 7 to 8. It will be understood that use of certain of the foregoing excipients, carriers, or stabilizers will result in the formation of cyclic polypeptide salts. While the preferred route of administration is by injection, other methods of administration are also anticipated such as intravenously (bolus and/or infusion), subcutaneously, intramuscularly, colonically, rectally, nasally or intraperitoneally, employing a variety of dosage forms such as suppositories, implanted pellets or small cylinders, aerosols, oral dosage formulations and topical formulations such as ointments, drops and dermal patches. The compounds are desirably incorporated into shaped articles such as implants which may employ inert materials such as biodegradable polymers or synthetic silicones, for example, Silastic, silicone rubber or other polymers commercially available.

The compounds may also be administered in the form of liposome delivery systems, such as small unilamellar vesicles, large unilamellar vesicles and multilamellar vesicles. Liposomes can be formed from a variety of lipids, such as cholesterol, stearylamine or phosphatidylcholines.

The compounds may also be delivered by the use of antibodies, antibody fragments, growth factors, hormones, or other targeting moieties, to which the compound molecules are coupled. The compounds may also be coupled with suitable polymers as targetable drug carriers. Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the platelet aggregation inhibitors may be coupled to a class of biodegradable polymers useful in achieving controlled release of a drug, for example polylactic acid, polyglyolic acid, copolymers of polylactic and polyglycolic acid, polyepsilon caprolactone, polyhydroxy butyric acid, polyorthoesters, polyacetals, polydihydmpyrans, polycyanoacrylates and cross linked or amphipathic block copolymers of hydrogels. Polymers and semipermeable polymer matrices may be formed into shaped articles, such as valves, stents, tubing, prostheses and the like.

Therapeutic compound liquid formulations generally are placed into a container having a sterile access port, for example, an intravenous solution bag or vial having a stopper pierceable by hypodermic injection needle.

Therapeutically effective dosages may be determined by either in vitro or in vivo methods. For each particular compound and formulation, individual determinations may be made to determine the optimal dosage required. The range of therapeutically effective dosages will naturally be influenced by the route of administration, the therapeutic objectives, and the condition of the patient. For injection by hypodermic needle, it may be assumed the dosage is delivered into the body's fluids. For other routes of administration, the absorption efficiency must be individually determined for each inhibitor by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be within the ambit of one skilled in the art Typically, applications of compound are commenced at lower dosage levels, with dosage levels being increased until the desired effect is achieved.

A typical dosage might range from about 0.001 mg/kg to about 1000 mg/kg, preferably from about 0.01 mg/kg to about 100 mg/kg, and more preferably from about 0.10 mg/kg to about 20 mg/kg. Advantageously, the compounds or formulations may be administered several times daily, in a once daily dose, or in other dosage regimens.

Typically, about 0.5 to 500 mg of a compound or mixture of compounds, as the free acid or base form or as a pharmaceutically acceptable salt or prodrug derivative (including esters), is compounded with a physiologically acceptable vehicle, carrier, excipient, binder, preservative, stabilizer, dye, flavor etc., as called for by accepted pharmaceutical practice. The amount of active ingredient in these compositions is such that a suitable dosage in the range indicated is obtained.

Typical adjuvants which may be incorporated into tablets, capsules and the like are a binder such as acacia, corn starch or gelatin, and excipient such as microcrystalline cellulose, a disintegrating agent like corn starch or alginic add, a lubricant such as magnesium stearate, a sweetening agent such as sucrose or lactose, or a flavoring agent. When a dosage form is a capsule, in addition to the above materials it may also contain a liquid carrier such as water, saline, a fatty oil. Other materials of various types may be used as coatings or as modifiers of the physical form of the dosage unit Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

The compounds and formulations may be used alone or in combination, or in combination with other therapeutic or diagnostic agents. In certain preferred embodiments, the compounds and/or formulations may be coadministered along with other compounds typically prescribed for these conditions according to generally accepted medical practice, such as anticoagulant agents, thrombolytic agents, or other antithrombotics, including platelet aggregation inhibitors, tissue plasminogen activators, urokinase, prourokinase, streptokinase, heparin, aspirin, or warfarin. The compounds and formulations can be utilized in vivo, ordinarily in mammals such as primates, such as humans, sheep, horses, cattle, pigs, dogs, cats, rats and mice, or in vitro.

The compounds, selected and used as disclosed herein, are believed to be useful for preventing or treating a condition characterized by undesired thrombosis, such as (a) the treatment or prevention of any thrombotically mediated acute coronary syndrome including myocardial infarction, unstable angina, refractory angina, occlusive coronary thrombus occurring post-thrombolytic therapy or post-coronary angioplasty, (b) the treatment or prevention of any thrombotically mediated cerebrovascular syndrome including embolic stroke, thrombotic stroke or transient ischemic attacks, (c) the treatment or prevention of any thrombotic syndrome occurring in the venous system including deep venous thrombosis or pulmonary embolus occurring either spontaneously or in the setting of malignancy, surgery or trauma, (d) the treatment or prevention of any coagulopathy including disseminated intravascular coagulation (including the setting of septic shock or other infection, surgery, pregnancy, trauma or malignancy and whether associated with multi-organ failure or not), thrombotic thrombocytopenic purpura, thromboanginitis obliterans, or thrombotic disease associated with heparin induced thrombocytopenia, (e) the treatment or prevention of thrombotic complications associated with extracorporeal circulation (e.g. renal dialysis, cardiopulmonary bypass or other oxygenation procedure, plasmapheresis), (f) the treatment or prevention of thrombotic complications associated with instrumentation (e.g. cardiac or other intravascular catheterization, intra-aortic balloon pump, coronary stent or cardiac valve), and (g) those involved with the fitting of prosthetic devices.

Without further description, it is believed that one of ordinary skill in the art can, using the preceding description and the following illustrative examples, make and utilize the compounds disclosed herein and practice the claimed methods. The following working examples therefore, specifically point out preferred embodiments, and are not to be construed as limiting in any way the remainder of the disclosure.

EXAMPLES

Example 1

Production of 2-Ethxoycarbonyl-4-oxo-4H-benzopyran (Ethyl 4-Oxochromene-2-carboxylate)

In a mixture containing 180 g of toluene and 12.0 g of diethyl oxalate was dissolved 30 g of 2-hydroxyacetophenone, to which 65.0 g of a 20% solution of sodium ethylate in ethanol was added dropwise. After completion of the reaction 13 g of 98% sulfuric acid was subsequently added, and the mixture was stirred at 60° C. for about 30 minutes. Then 140 g of water was added, and the mixture was subjected to separation of the organic layer. The resultant organic layer was concentrated, after which 55.0 g of hexane was added and the mixture was filtered below 10° C. which yields about 34.0 g of ethyl 4-oxochromene-2-carboxylate. (Approximately 95% yield).

Example 2

Production of Ethyl 4-Oxochromane-2-carboxylate

A hydrogenator was charged by adding 6 g of ethyl 4-oxochromene-2-carboxylate, 3.5 mL of acetic anhydride, 1 g of 10% palladium on carbon, 4.0 g of dried 3A molecular sieves (powered), and 30 mL of glacial acetic acid. After purging several times with nitrogen, the hydrogenator was purged several times with hydrogen. While maintaining stirring the reaction mixture was pressurized to about 30 psi of hydrogen, heated to about 60° C. and maintained under those conditions for about 10–12 hours. HPLC monitoring of the reaction was used to determine when the reaction was essentially complete, e.g., when the area ratio by HPLC between the chromen-4-one and the chroman-4-one was not more than 3%. The mixture was then cooled to room temperature and filtered through a celite bed. The catalyst and sieves were washed with 10 mL aliquots of glacial acetic acid and the washes were combined with the filtrate. The combined mixture was concentrated under mild distillation conditions to an oil, which was dissolved with ethyl acetate and extracted with saturated $NaHCO_3$. After the extraction, the aqueous layer was washed with ethyl acetate and the mixture neutralized to a low pH with concentrated HCl. The mixtures was extracted several times with ethyl acetate, the extracts were combined, concentrated to a solid, washed with acetonitrile and then filtered. Upon drying, about 3.5–4.0 grams of ethyl 4-oxo-chromane-2-carboxylate were obtained as a solid.

Example 3

Production of Ethyl 6-Nitro-4-oxochromane-2-carboxylate

To a sulfuric acid solution of the ethyl 4-oxochromane-2-carboxylate of Example 2 at −10° C. (about 3 ml) was added potassium nitrate in sulfuric acid (about 1 ml), wherein the molar ratio of the potassium nitrate starting material to the chromone compound starting material was slightly in excess of 1:1. The reaction mixture was stirred at about 0° C. for 1 hour, the ice bath was removed and the reaction mixture was stirred at room temperature for 46 hours. The nitrated chromone compound forms a precipitate and the reaction was maintained at room temperature until monitoring of the solution with HPLC shows the solution to be essentially free of the chromone starting material (less than 3%). The reaction mixture was poured into ice and the precipitate was extracted with ethyl acetate. The ethyl acetate layer was dried, filtered and evaporated to give a light yellow solid. The yield of ethyl 6-nitro-4-oxochromane-2-carboxylate was approximately 80%.

Example 4

Production of Ethyl 6-Nitro-4-oxochromane-2-carboxylate

In a mixture containing 1 mole of 4-nitrophenol were added 2 moles of diethyl diester of maleic add and 1120 ml methane sulfonic acid. The mixture was then heated to 92° C. for 20 hours. The reaction was cooled to 0° C., poured onto 2 liters of ice and 2 liters of water and extracted with 3 times with 800 mls of diethyl ether. The organic layers were combined, washed with 3×500 ml water, 4×500 ml 1N NaOH, 2×500 ml water, and 500 ml brine, dried over magnesium sulfate and concentrated under vacuum to yield about 50–60 g of crude yellow solid, which was ethyl 6-nitro-4-oxochromane-2-carboxylate. (Approximately 45%–65% yield).

Example 5

In Situ Ester Production of Ethyl 6-Nitro-4-oxochromane-2-carboxylate

In a mixture containing 1 mole of 4-nitrophenol was added 2 moles of maleic acid and 500 mL of 1N sulfuric acid. The mixture was then heated to 92° C. for 10–20 hours and monitored by HPLC for completion of the reaction with respect to the nitrophenol starting material. The reaction was cooled to 50° C. and 2 moles of ethanol were added. The temperature maintained between 40° C.–55° C. for 1–3 hours or until HPLC indicates that the esterification was complete. The reaction was cooled to 0° C., poured onto 2 liters of ice and 2 liters of water and extracted with 3 times with 800 mls of diethyl ether (or ethanol). The organic layers were combined, washed with 3×500 ml water, 4×500 ml 1N NaOH, 2×500 ml water, and 500 ml brine, dried over magnesium sulfate and concentrated under vacuum to yield about 75 g of crude yellow solid, which was ethyl 6-nitro-4-oxochromane-2-carboxylate. (Approximately>60–75% yield).

Example 6

Production of Ethyl 2-(4-Oxo-chromen-2-yl) Acetate

In a mixture containing 1 mole of phenol was added 1.5 moles of beta-keto glutaric acid, 500 mL of 1N sulfuric acid and 200 mL of ethanol. The mixture was then heated to 80° C. for 10–20 hours and monitored by HPLC for completion of the reaction with respect to the phenol starting material. The reaction was cooled to 0° C. and poured onto 2 liters of ice and 2 liters of water and extracted with 3 times with 800 mls of diethyl ether (or ethanol). The organic layers were combined, washed with 3×500 ml water, 4×500 ml 1N NaOH, 2×500 ml water, and 500 ml brine, dried over magnesium sulfate and concentrated under vacuum to yield about 60–70 g of a crude yellow solid, which was ethyl 2-(4-oxo-chromen-2-yl) acetate. (Approximately>55–65% yield).

Example 7

Production of Ethyl 2-(6-Nitro-4-oxo-2-yl) Acetate

The crude mixture obtained in Example 6 was reduced using 10% palladium on carbon substantially as set forth in Example 2, above, and then nitrated substantially as set forth in Example 3, above, to yield a racemate of ethyl 2-(6-nitro-4-oxo-chroman-2-yl) acetate. (Approximately>80% yield with respect to the amount of starting material obtain from Example 6).

Example 8

Production of 6-Nitro-chromen-4-one

One gram molecular weight of 4-oxo-[4H]-benzopyran (Aldrich Catalog Number 19,922-2), i.e., chromen-4-one, was nitrated and recovered using the procedures set forth in Example 3, above, to yield about 92 g of 6-nitro-chromen-4-one, approximately 60% yield with respect to the starting material.

Example 9

Production of Benzopyrilium Salt of 6-Nitro-chromen-4-one

The crude material of Example 8 was reacted with TBSOTf under standard salt-forming conditions to yield the benzopyrilium salt in about 95% yield.

Example 10

Production of Ethyl 2-(4-[TBS-enol]-6-nitro-chroman-2-yl) Acetate

The benzopyrilium salt of Example 9 was reacted with a molar excess of the ketene enol resulting from TBSOTf reaction with the ethyl ester of acetic acid, by adding the ketene enol dropwise to the benzopyrilium salt dropwise to produce the product in a 90% yield based upon the benzopyrilium salt starting material.

Example 11

Production of Ethyl 2-(6-nitro-4-oxo-chroman-2-yl) Acetate

The 4[TBS-enol] of Example 10 was converted to the ketone by acidify the reaction mixture with HCl and allowing the reaction mixture to come to room temperature while stirring for 4–6 hours and the reaction mixture was cooled over ice. The precipitate crystals were separated extracted with ethyl acetate. The ethyl acetate layer was dried and filtered to yield a light yellow solid in about 85–90% yield with respect to the benzopyrilium salt starting material of Example 9. The light yellow solid was the racemate of ethyl 2-(6-nitro-4-oxo-chroman-2-yl) acetate.

Example 12 which follows provides a specific example of enzymatic resolution. However, this process may be used for compounds having different acid chain lengths and different ester groups, and may also be used for different types of lipase enzymes.

Example 12

Enymatic Resolution of Ethyl 2-(6-nitro-4-oxo-chroman-2-yl) Acetate Racemate Approximately 330 g of the ethyl 2-(6-nitro-4-oxo-chroman-2-yl) acetate racemate of Example 11 was placed in isopropyl alcohol and water in the presence of 1 g of the lipase enzyme ChiroCLEC-PC (Altus, Inc.) under the conditions set forth in the ChiroCLEC-PC Information Booklet available from Altus for 24 hours. After separation of the free acid product from the ester substrate, approximately 160 gm of the 2–2S6-nitro-4-oxochroman-2-yl-acetic acid was obtained in 98.5% purity.

Examples 13 and 14, which follow, provide a specific example of conversion of a 6-nitro-4-oxo-chroman-2-yl add to a 6-amino-chroman-2-yl add ester salt. The procedures of these examples may be used for compounds having esters other than ethyl and acid groups other than acetic. In addition, adds and their corresponding esters as well as salts and their corresponding free bases may be interconverted using methods known to those skilled in the art.

Example 13

Production of 2-[2S) 6-Acetamido-chroman-2-yl] Acetic Acid

A hydrogenator was charged by adding 6 g of 2-[(2S) 6-nitro-4-oxo-chroman-2-yl] acetic acid, 3.5 mL of acetic anhydride, 1 g of 10% palladium on carbon, 4.0 g of dried 3A molecular sieves (powered), and 30 mL of glacial acetic acid. After purging several times with nitrogen, the hydrogenator was purged several times with hydrogen. While maintaining stirring the reaction mixture was pressurized to about 70 psi of hydrogen, heated to about 80° C. and maintained under those conditions for about 10–12 hours. The bomb was then cooled to about 50° C., evacuated of hydrogen and purged several times with nitrogen. Trifluroroacetic acid (3.5 mL) was added the bomb, the bomb was resealed, was purged several times with hydrogen and was then pressurized to 70 psi of hydrogen. The reaction mixture was stirred as it was heated to 80° C. and was maintained at 80° C. with stirring. HPLC monitoring was used to determine when the reaction was essentially completed (the area ratio by HPLC between the intermediate and product was not more than 3%) and the mixture was cooled to room temperature. After filtering of the mixture through a celite bed, the catalyst and sieves were washed with 10 mL aliquots of glacial acetic acid and the washes combined with the filtrate. The combined mixture was concentrated under mild distillation conditions to an oil, which was dissolved with ethyl acetate and extracted with saturated $NaHCO_3$. After the extraction, the aqueous layer was washed with ethyl acetate and the mixture neutralized to a low pH with concentrated HCl. The mixtures was extracted several times with ethyl acetate, the extracts were combined, concentrated to a solid, washed with acetonitrile and then filtered. Upon drying, about 3.5–4.0 grams of ethyl 2-((2S)-6-acetamido-chroman-2-yl) acetate were obtained as a white solid.

Example 14

Production of Hydrochloride Salt of Ethyl 2-((2S) 6-Amino-chroman-2-yl) Acetate A mixture of 1.5 g of the ethyl 2-((2S)-6-acetamido-chroman-2-yl) acetate of Example 13, above, in 25 mL of concentrated sulfuric acid was stirred vigorously at room temperature for about 6 hours, 50 mL of ethanol was added and the mixture was allowed to sit overnight. The precipitate was recovered by filtration and rinsed with 50 mL aliquots of ether and dried. Absolute ethanol (25 mL) and HCl (10 mL) were mixed with the precipitate for 2 hours followed by addition of 10 mL of concentrated HCl. The precipitate was recovered and recrystallized twice in an ether/isopropanol solvent mixture. Yielded was about 1.4 g of ethyl 2-((2S)-6-amino-chroman-2-yl) acetate hydrochloride (about 85–90% yield).

Example 15

Production of Ethyl 2-(6-Nitro-4-oxo-chroman-2-yl) Acetate Recemate

Approximately 330 g of the ethyl 2-((2R)-6-nitro-4-oxo-chroman-2-yl) acetate of Example 12 was separated in 99.4% purity from the (2S) isomer. To the (2R) enantiomer ester was added 500 mL of ethanol and a catalytic amount of potassium ethanolate (<1 equivalent). The mixture was maintained at room temperature for 28 hours with stirring. Saponification was performed by addition of aqueous 1 N NaOH in ethanol for 3 hours. After acidification with 1N aqueous hydrochloric acid the 6-nitro-4-oxochroman-2-yl acetic acid racemate was recovered as a precipitate in approximately 80% yield (about 250 g) with respect to the (2R) enantiomer ester starting material.

Example 16

Production of Ethyl 2-(6-Nitro-4-oxo-chroman-2-yl) Acetate Recemate

About 2.5 g of the crude precipitate of Example 15 was recovered and added to 40 mL of concentrated sulfuric acid with vigorous stirring at room temperature for about 6 hours, 75 mL of ethanol was added and the mixture was allowed to sit overnight. The precipitate was recovered by filtration and rinsed with 60 mL aliquots of ether and dried. Absolute ethanol (40 mL) and HCl (20 mL) were mixed with the precipitate for 2 hours. The precipitate was recovered and recrystallized twice in an ether/isopropanol solvent mixture. About 2.4 g of the ethyl 2-(6-nitro-4-oxo-chroman-2-yl) acetate racemate was recovered (about 85–90% yield), which can be recycled to Example 12 for enzymatic resolution of the enantiomers and a higher overall recovery of the (2S) enantiomer.

Examples 17–19 describe a specific procedure for lengthening a 2-carboxyl chain on a chroman-4-one by one carbon. The procedure may be adapted to lengthen the chain by more than one carbon, including two carbons and three carbons, by the use of appropriate reagents.

Example 17

Production of 2-(Hydroxymethy)-chroman-4-one

The carboxylic acid group of the compound of Example 2 (ethyl 4-oxochromane-2-carboxylate) was treated with a metallic hydroxide base in ethanol, and then the aqueous layer was treated with an acid to form the free acid, which was washed with water and then dried to yield 3 g of 4-oxo-chromane-2-carboxylic acid.

The 3 g of 4-oxo-chromane-2-carboxylic acid in THF (65 mL) was stirred was cooled to 0° C. and borane-methyl sulfide complex (2.5 mL of M solution, 25 mmoles) was added dropwise for about 15 minutes. The solution was warmed to room temperature and then heated at reflux for 4 hours. The solution was cooled to room temperature and 10% aqueous hydrochloric acid (20 mL) was added over 15 minutes and the solution was stirred at room temperature for 2 hours. The mixture was concentrated to approximately 25 mL. The solution was poured into ethyl acetate (50 mL) and washed with water (2×30 mL), saturated sodium bicarbonate (2×30 mL) and saturated ammonium chloride (2×30 mL). The organic layer was separated dried over anhydrous MgSO4, and then concentrated in vacuo to yield about 2.6 g of 2-(hydroxymethyl)-chroman-4-one (86.7% yield)

Example 18

Production of 2-Cyanomethylchromen-4-one

To a solution of 2.0 g of 2-(hydroxymethyl)-chroman-4-one (from Example 17) in 35 mL of $CH_2Cl_2$ and 1.5 mL of pyridine was added 2 g p-toluenesulfonylchloride. The mixture was stirred at 25° C. for 36 hours, then diluted with 20 mL ether and washed with 10 mL. The organic layer was dried over $MgSO_4$ and concentrated to give 3.4 grams of crude tosylate. To the crude tosylate in 20 mL of DMSO was added with stirring 80 mg of powdered sodium cyanide and the mixture was heated to reflux for 1.5 hours under an inert atmosphere. The cooled mixture was diluted with 50 mL of water and extracted with 6 100 mL portions of ether and the ether extracts were dried over anhydrous MgSO4 and filtered. The filtrate was concentrated and the residue was recrystallized with ether/isopropanol to yield 1.7 grams of 2-cyanomethylchroman-4-one.(about 85% yield).

Example 19

Production of Ethyl 2-(4-Oxochroman-2-yl) Acetate

A mixture of 1.5 g of 2-cyanomethylchroman 4one (Example 20) in 25 mL of concentrated hydrochloric add was stirred vigorously at room temperature for about 6 hours, 50 mL of ethanol was added and the mixture was allowed to sit overnight. The precipitate was recovered by filtration and rinsed with 50 mL aliquots of ether and dried. Absolute ethanol (25 mL) and HCl (10 mL) were mixed with the precipitate for 2 hours followed by addition of 10 mL of concentrated HCl. The precipitate was recovered and recrystallized twice in an ether/isopropanol solvent mixture. Yielded was about 1.3 g of ethyl 2-(4-oxo-chroman-2-yl) acetate (about 80% yield).

Example 20

Production of Ethyl 2-(6-Nitro-4-oxo-chroman-2-yl) Acetate, Racemate

The 1.3 g of the ethyl 2-(4-oxo-chroman-2-yl) acetate, racemate (from Example 19) was nitrated using generally the procedures described in Example 3 to yield 1.04 g of ethyl 2-(6-nitro-4-oxo-chroman-2-yl) acetate (80% yield).

Example 21

Production of Ethyl 2-[(2S) 6-Nitro-4-oxo-chroman-2-yl] Acetate

The racemate of Example 20 was resolved into the respective enantiomers using the procedures in Example 12 to separate out the (2S) enantiomer. Alternatively, the free acid was formed and an esterification was performed in the present of the lipase as describe in the ChiroCLEC-PC Information Booklet from Altus for 24 hours and the (2R) enantiomer was obtained instead of the (2S) enantiomer. Either enantiomer was obtained in 98.5% purity.

Example 22

Production of Ethyl 2-(6-Nitro-4-oxo-chroman-2-yl) Acetate Racemate From an Enriched Ethyl 2-[(2R>2S) 6-Nitro-4-oxo-chroman-2-yl] Acetate Composition Approximately 330 g of the ethyl ester of 2-[(2R>2S) nitro-4-oxo-chroman-2-yl] acetic acid of Example 12 was separated in about 98 purity for the (2R) isomer from the (2S) isomer. To the (2R) enantiomer ester was added 500 mL of ethanol and a catalytic amount of potassium ethoxide (<1 equivalent). The mixture was maintained at room temperature for 28 hours with stirring. Saponification was performed by addition of aqueous 1 N NaOH in ethanol for 3 hours. After acidification with 1N aqueous hydrochloric acid the racemic (2S approximately equal to 2R) 2-(6-nitro-oxo-chroman-2-yl) acetic acid was recovered as a precipitate in approximately 80% yield (about 250 g) with respect to the (2R) enantiomer ester starting material. The ethyl 2-(6-nitro-4-oxo-chroman-2-yl) acetate racemate was formed from the free acid using the general esterification procedures as set forth in Example 14, above, which can be recycled to Example 12 for enzymatic resolution of the enantiomers and a higher overall recovery of the (2S) enantiomer.

The procedures in the above examples directed to resolution of the 6-nitro substituted ethyl ester of the acetic acid (2S or 2R) chromanyl enantiomer from the racemate, can readily be adapted to resolution of the acetamido derivatives of the same structures and to nitro position isomers, as well as homologs of the compounds. For example, the enzymatic resolution procedures of Example 12, may be readily adapted to the acetamido derivatives The procedures above may be altered to use different starting materials, such as those having different substituents at the 6-position (amino, protected amino, hydrogen, etc.) Additionally, other minor modifications may be done, such as substitution of other known reagents, other catalysts, etc. Furthermore, other alcohols may be used to make other esters, or the esters may be hydrolyzed to provide the free acid.

In view of the above description it is believed that one of ordinary skill can practice the invention. The examples given above are non-limiting in that one of ordinary skill in view of the above will readily envision other obvious permutations and variations without departing from the principal concepts embodied therein. Such permutations and variations are also within the scope of the disclosure.

What is claimed is:

1. A process for making a compound, or a salt thereof, having a general formula:

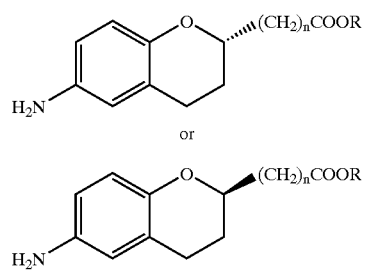

wherein R is $C_1$–$C_8$ alkyl and n=0 to about 3, comprising:

(a) reacting phenol and beta-keto glutaric acid in $H_2SO_4$ and ethanol with heat to create a reaction mixture, followed by pouring the reaction mixture onto ice water, extracting a chromenone product formed from (a) into an organic solvent and evaporating the organic solvent as follows:

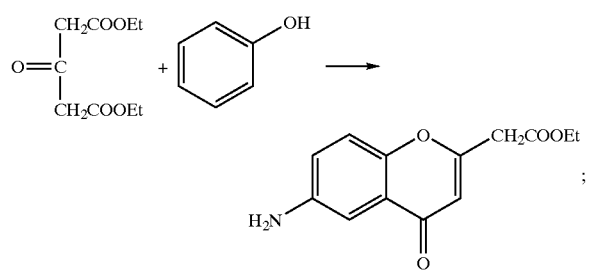

(b) hydrogenating the chromenone product from (a) above to produce a corresponding chromanone:

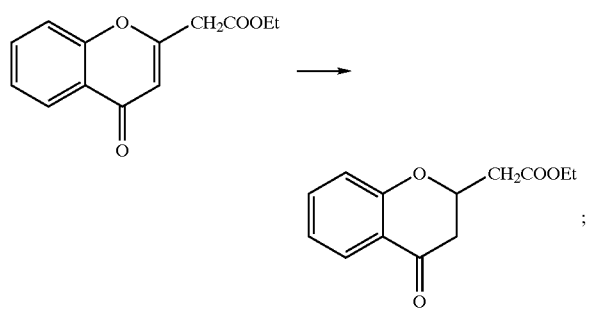

(c) nitrating the chromanone from (b) to create a racemic mixture as follows:

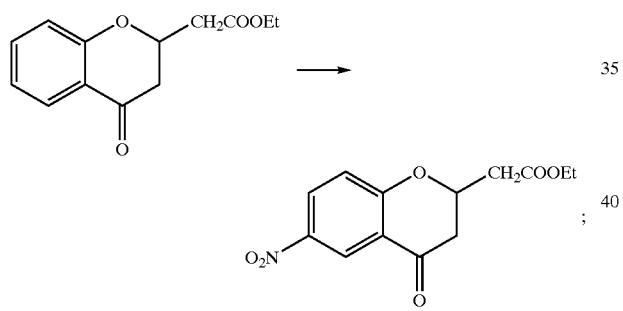

(d) resolving the racemic mixture using a lipase enzyme, as follows:

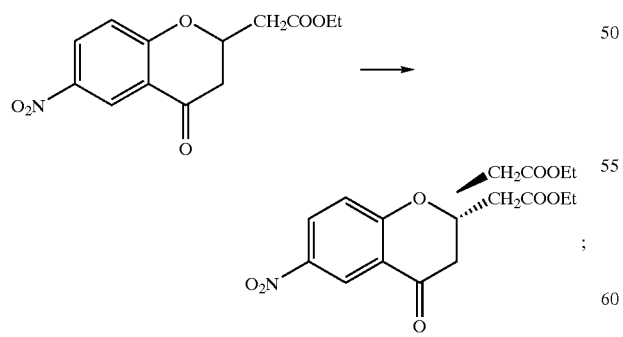

(e) hydrogenating the product from (d) to convert the oxo group to a methylene group and convert the nitro group to an amino group and subsequently protecting the amino group as an acetamido group as follows:

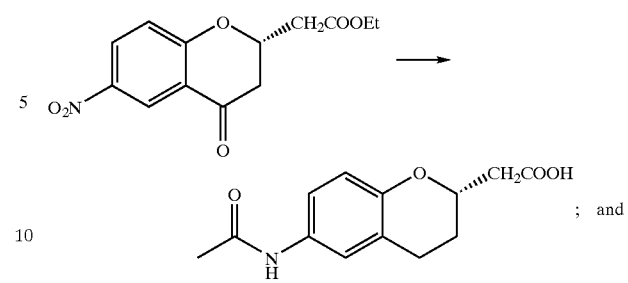

(f) acidifying the product from (e) above to form an amine followed by addition of concentrated HCl to the amine to produce an HCl salt of the amine as follows:

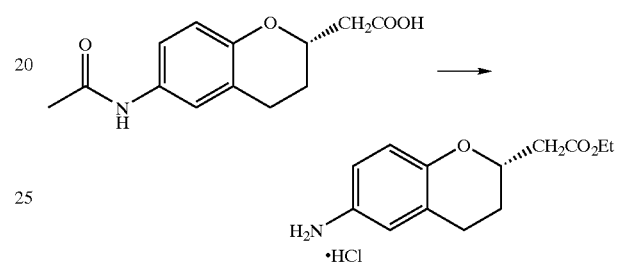

2. A process for making a compound, or a salt thereof, having a general formula:

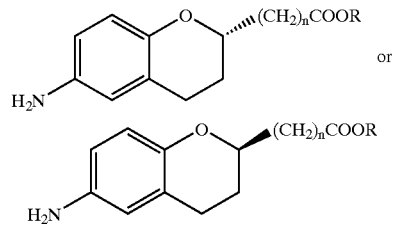

wherein R is $C_1$–$C_8$ alkyl and n=0 to about 3, comprising:

(a) reacting 2-hydroxyacetophenone and diethyloxalate in the presence of sodium ethoxide followed by addition of concentrated sulfuric acid to form a chromen-4-one as follows:

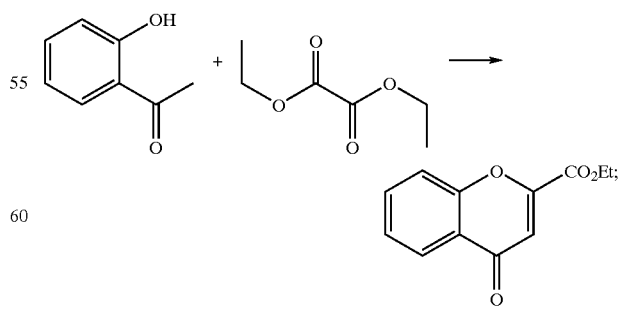

(b) hydrogenating the chromen-4-one to form a chroman-4-one as follows:

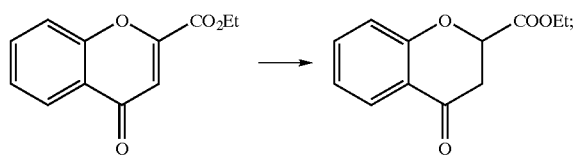

(c) performing a chain extension on the product from (b) by first forming a free acid from the ester, followed by reacting the free acid with borane-methyl sulfide complex to form a 2-hydroxymethyl derivative, followed by replacing the hydroxy group with a tosyl group and reacting the tosyl derivative with a cyanide salt to form a 2-cyano derivative, followed by hydrolyzing the cyano derivative in concentrated acid to form a 2-acid group and esterifying the 2-acid group as follows:

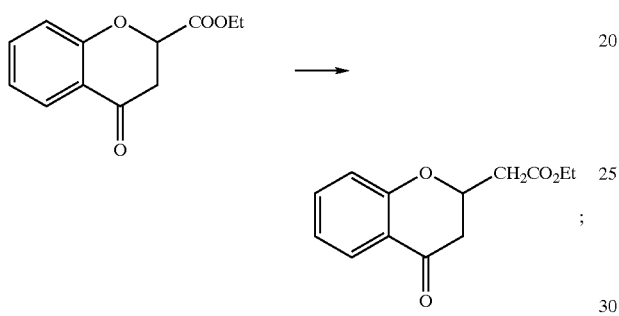

(d) nitrating the product from (c) above to form a 6-nitro group as part of a racemic mixture as follows:

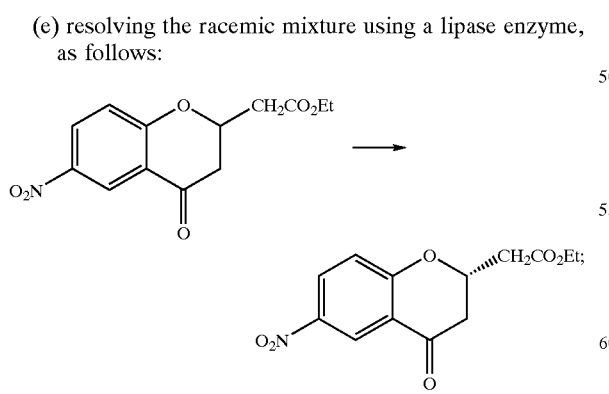

(e) resolving the racemic mixture using a lipase enzyme, as follows:

(f) hydrogenating the product from (e) to convert the oxo group to a methylene group and convert the nitro group to an amino group and subsequently protecting the amino group as an acetamido group as follows:

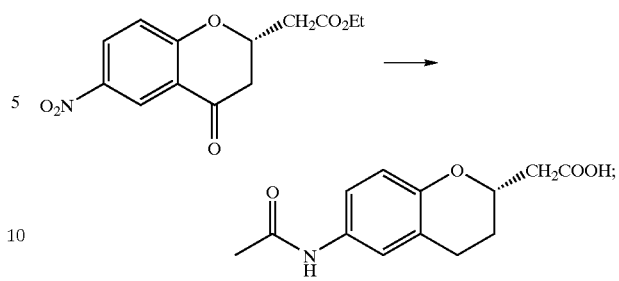

(g) acidifying the product from (f) above to form an amine followed by addition of concentrated HCl to the amine to produce an HCl salt of the amine as follows

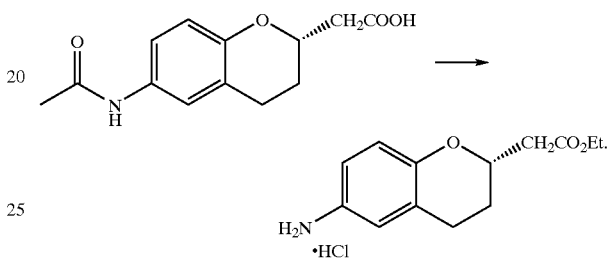

3. A process for making a compound, or a salt thereof, having a general formula:

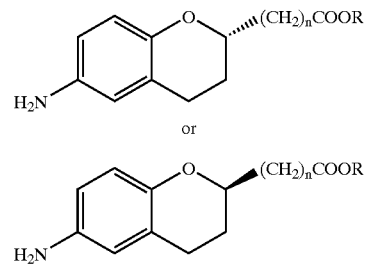

wherein R is $C_1$–$C_8$ alkyl and n=0 to about 3, comprising:

(a) reacting nitrophenol and diethyl ester of maleic acid with methane sulfonic acid under heating as follows:

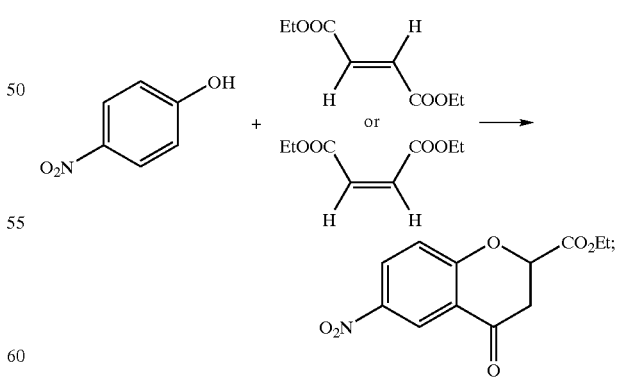

(b) performing a chain extension on the product from (a) by first making a free acid from the ester, followed by the free acid reacting with borane-methyl sulfide complex to form a 2-hydroxymethyl derivative, followed by replacing the hydroxy group with a tosyl group and reacting the tosyl derivative with a cyanide salt to form a 2-cyano derivative, followed by hydrolyzing the cyano derivative in concentrated acid to form a 2-acid group and esterifying the 2-acid group as follows:

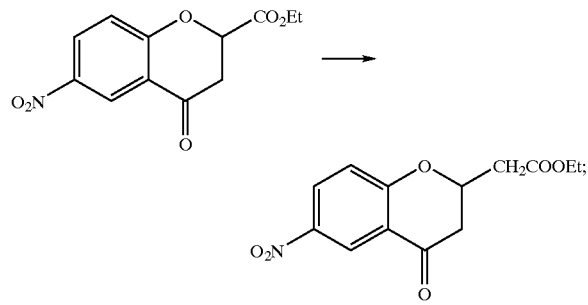

(c) resolving the racemic mixture using a lipase enzyme, as follows:

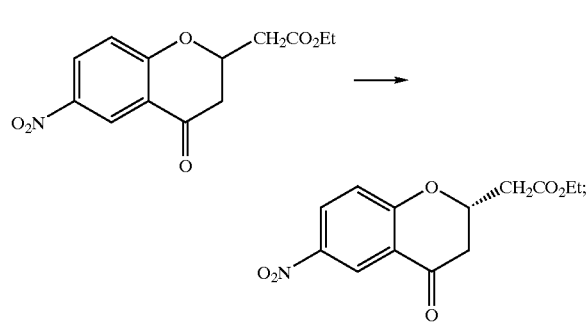

(d) hydrogenating the product from (c) to convert the oxo group to a methylene group and convert the nitro group to an amino group and subsequently protecting the amino group as an acetamido group as follows:

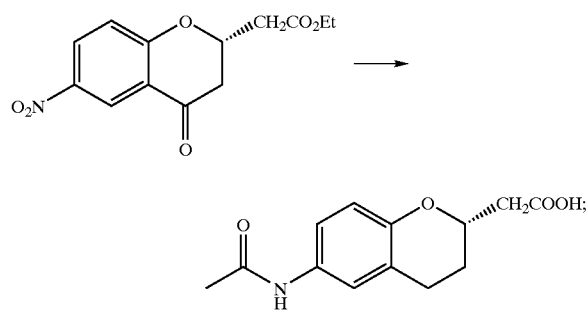

(e) acidifying the product from (d) above to form an amine followed by addition of concentrated HCl to the amine to produce an HCl salt of the amine as follows:

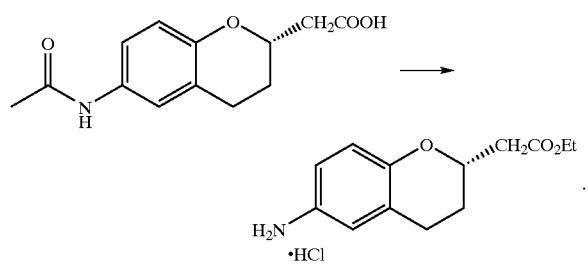

4. A process for making a compound, or a salt thereof, having a general formula:

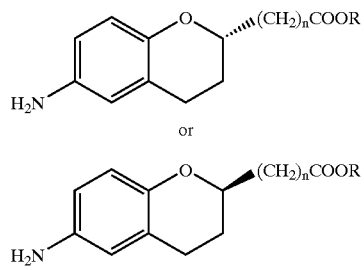

wherein R is $C_1$–$C_8$ alkyl and n=0 to about 3, comprising:

(a) nitrating the chromen-4-one at the 6-position as follows:

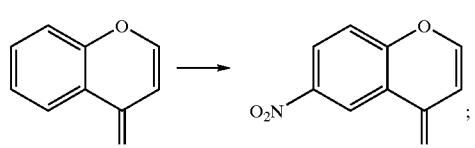

(b) reacting the product from (a) above with TBSOTf to form a benzopyrillium salt as follows:

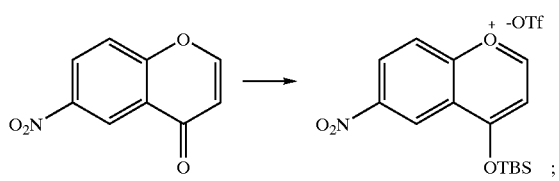

(c) adding a ketene enol to the benzopyrillium salt from (b) above as follows:

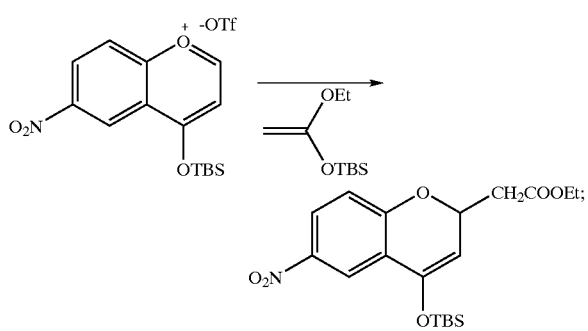

(d) acidifying the product from (c) above to remove the TBS group at the 2-position on the 6-nitro-4-oxochromane ring to form a racemic mixture as follows:

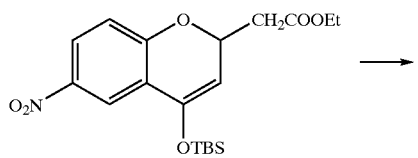

-continued

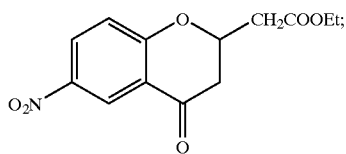

(e) resolving the racemic mixture using a lipase enzyme, as follows:

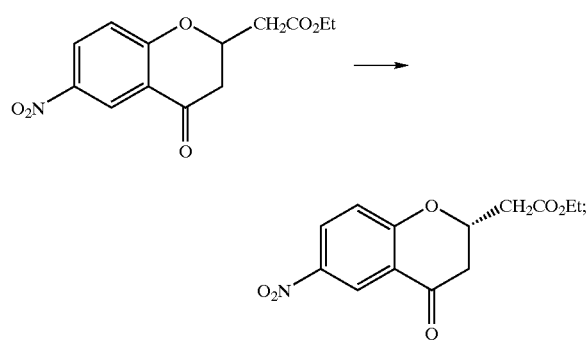

(f) hydrogenating the product from (e) to convert the oxo group to a methylene group and convert the nitro group to an amino group and subsequently protecting the amino group as an acetamido group as follows:

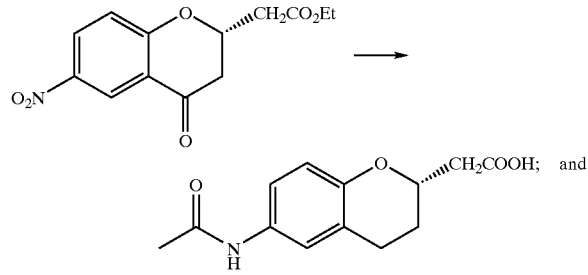

(g) acidifying the product from (f) above to recover an amine followed by addition of concentrated HCl to the amine to produce an HCl salt of the amine as follows:

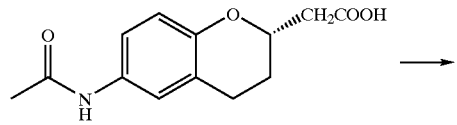

-continued

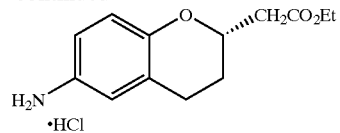

5. A composition produced by a method of claim 1, comprising about 75% to about 100% of a single (2R) or (2S) enantiomer of 6-aminochroman-2-yl acetic acid or an ester thereof.

6. A process according to claim 1 wherein the enzyme is a lipase from *Pseudomonas cepacia*.

7. A process according to claim 6 wherein the lipase is ps 30 lipase.

8. A process according to claim 1, wherein the lipase is a lipase stabilized by cross-linking with alpha keto glutarate.

9. A process according to claim 8, wherein the enzyme is stabilized ps 30 enzyme ChiroCLEC-PC.

10. A composition produced by a method of claim 2, comprising about 75% to about 100% of a single (2R) or (2S) enantiomer of 6-aminochroman-2-yl acetic acid or an ester thereof.

11. A process according to claim 2 wherein the enzyme is a lipase from *Pseudomonas cepacia*.

12. A process according to claim 11, wherein the lipase is PS 30 lipase.

13. A process according to claim 2, wherein the lipase is a lipase stabilized by cross-linking with alpha keto glutarate.

14. A process according to claim 13, wherein the enzyme is stabilized PS 30 enzyme ChiroCLEC-PC.

15. A composition produced by a method of claim 3, comprising about 75% to about 100% of a single (2R) or (2S) enantiomer of 6-aminochroman-2-yl acetic acid or an ester thereof.

16. A process according to claim 3 wherein the enzyme is a lipase from *Pseudomonas cepacia*.

17. A process according to claim 16, wherein the lipase is PS 30 lipase.

18. A process according to claim 3, wherein the lipase is a lipase stabilized by cross-linking with alpha keto glutarate.

19. A process according to claim 18, wherein the enzyme is stabilized PS 30 enzyme ChiroCLEC-PC.

20. A composition produced by a method of claim 4, comprising about 75% to about 100% of a single (2R) or (2S) enantiomer of 6-aminochroman-2-yl acetic acid or an ester thereof.

21. A process according to claim 4 wherein the enzyme is a lipase from *Pseudomonas cepacia*.

22. A process according to claim 21, wherein the lipase is PS 30 lipase.

23. A process according to claim 4, wherein the lipase is a lipase stabilized by cross-linking with alpha keto glutarate.

24. A process according to claim 23, wherein the enzyme is stabilized PS 30 enzyme ChiroCLEC-PC.

* * * * *